United States Patent [19]

Morgan et al.

[11] Patent Number: 4,871,392
[45] Date of Patent: Oct. 3, 1989

[54] AQUEOUS SUSPENSION CONCENTRATE COMPOSITIONS OF PENDIMETHALIN

[75] Inventors: Leonard J. Morgan; Mark Bell, both of Hampshire, England

[73] Assignee: American Cyanamid Company, Stamford, Conn.

[21] Appl. No.: 45,457

[22] Filed: May 7, 1987

Related U.S. Application Data

[63] Continuation-in-part of Ser. No. 867,106, May 23, 1986, abandoned.

[51] Int. Cl.$^4$ ............................................. A01N 53/06
[52] U.S. Cl. .................................... 71/121; 71/DIG. 1
[58] Field of Search ............................ 71/121, DIG. 1

[56] References Cited

U.S. PATENT DOCUMENTS

| | | |
|---|---|---|
| 3,948,636 | 4/1976 | Marks .............................. 71/DIG. 1 |
| 4,077,795 | 3/1978 | Cooke et al. ........................... 71/121 |
| 4,082,537 | 4/1978 | Dudkowski ........................... 71/121 |
| 4,188,202 | 2/1980 | Gillings et al. ......................... 71/88 |
| 4,266,965 | 5/1981 | Simons ............................ 71/DIG. 1 |
| 4,594,096 | 6/1986 | Albrecht et al. ............... 71/DIG. 1 |

Primary Examiner—Glennon H. Hollrah
Assistant Examiner—Mark W. Russell
Attorney, Agent, or Firm—Estelle J. Tsevdos

[57] ABSTRACT

The present invention relates to novel stable aqueous suspension concentrate compositions of the low-melting pesticide pendimethalin, alone or in combination with secondary pesticides which are water soluble or have melting points greater than 70° C. The invention also relates to methods for the preparation of these compositions. Uniquely, pendimethalin may be present in the compositions of the invention in a ratio of orange crystal form to yellow crystal form of 4:96 up to totally orange crystal form.

12 Claims, No Drawings

AQUEOUS SUSPENSION CONCENTRATE COMPOSITIONS OF PENDIMETHALIN

BACKGROUND OF THE INVENTION

Suspension concentrate or aqueous flowable pesticidal compositions are concentrated suspensions of water insoluble pesticides and mixtures of pesticides in aqueous systems. The present invention relates to stable such pendimethalin compositions.

Pendimethalin is a dinitroaniline that exists in polymorphic form, both in orange crystal form and yellow crystal form. U.S. Pat. Nos. 4,082,537 and 4,150,969 address pendimethalin's unique formulation problems and provide ways to avoid formation and/or presence of the larger, orange crystal form (both incorporated herein by reference). It is believed that the presence of pendimethalin in the orange macrocrystal form results in large elongated crystals in final formulations.

In order to formulate stable wettable powder compositions of pendimethalin, these two patents disclose utilizing a stabilized pendimethalin, stabilized by the addition of either sodium dialkyl ($C_6$-$C_8$) sulfosuccinate or an ethoxylated $\beta$-diamine. This technique maintains pendimethalin in the yellow crystal form which does not favor the formation of large elongated crystals in formulated product for the preparation of wettable powders. However, these patents fail to disclose ways to formulate pendimethalin as a stable suspension concentrate composition or aqueous flowable composition with orange crystal forms, which form is favored.

These aqueous compositions frequently contain about 10% to 80%, by weight of a solid pesticide or mixture of solid pesticides, thereby providing a method for handling those pesticides which are relatively water insoluble in an aqueous medium. Since these types of compositions have the desirable characteristics of a thick liquid, they may be poured or pumped. Thus, some of the problems, like dusting that is possible in solid compositions of wettable powders and granulars, are avoided. Further, these aqueous-based concentrates also have the added advantage of not requiring the use of organic solvents, often present in emulsifiable concentrates.

For these reasons, it is desirable to formulate pesticides into suspension concentrates or aqueous flowables. However, such formulations have their own problems such as gelling, caking and settling, as well as problems because of the physical and chemical characteristics of the pesticide or mixture of pesticides. Pendimethalin is one of these pesticides that is somewhat difficult to formulate.

Oftentimes, when pendimethalin in the orange macrocrystal form is found in compositions, very large, elongated crystals (about 3000 microns in length) appear in final product, resulting in instability, difficulty in processing and unreliability of usage. Thus, formulating compositions wherein these elongated crystals do not develop is crucial to stability and necessary to obtain even distribution of active compound for application.

The problems associated with the development of suspension concentrate compositions containing low melting active ingredients, alone or in combination with higher melting active ingredients, are described in German patent application No. DE 3302648 A1. German patent application No. DE 3302648 A1 tries to deal with the problems of an aqueous mixed dispersion of a low melting active ingredient in a solvent of phthalic acid $C_1$-$C_{12}$ alkyl esters in combination with an aqueous suspension concentrate containing one or more active ingredients as an alternative to a suspension concentrate containing low melting active ingredients, such as pendimethalin[N-(1-ethyl-propyl)-2,6-dinitro-3,4-xylidine]. The reason for the alternative approach of that application is the inability to prepare stable suspension concentrates by various techniques, including those of European patent application 0 33291.2 That EPO application describes insecticidal suspension concentrate compositions of phosalone and adjuvants which may be prepared with molten insecticidie. These references do not address ways helpful to the development of pendimethalin compositions which utilize the orange crystal form to produce a stable and evenly efficacious product.

It is an object of the present invention to provide stable aqueous concentrate compositions of the low melting pesticide, pendimethalin, in the orange crystal form either alone or in combination with secondary pesticide(s) in order to avoid the problem of formation of large elongated crystals of formulated pendimethalin. These secondary pesticides are often water insoluble or have melting points greater than 70° C.

It is a further object of this invention to provide such stable aqueous suspension concentrate compositions of pendimethalin having a ratio of orange crystal to yellow crystal of 4:96 to totally (100%) orange crystal form.

Furthermore, an additional object of the present invention is to provide methods for preparing such stable aqueous suspension concentrate compositions.

These and other objects will become more apparent by the detailed description of the invention provided herein.

SUMMARY OF THE INVENTION

The present invention relates to stable aqueous suspension concentrate compositions or aqueous flowable compositions comprising pendimethalin, alone or in combination with secondary pesticide(s). Preferred compositions of the invention comprise, on a weight to volume basis about 5.0% to 50.0% pendimethalin having an orange cyrstal to yellow crystal ratio of about 4/96 up to totally 100% orange crystal form; about 0% to 50.0% of one or more secondary pesticide(s); about 3.0% to 30.0% of coformulants, such as surfactants, dispersing agents, wetting agents, antifreezing agents, antifoaming agents, thickening agents, suspending agents, preservatives and the like which do not solubilize or dissolve the pendimethalin; and about 20.0% to 92.0% water.

DETAILED DESCRIPTION OF THE INVENTION

Preferred stable aqueous suspension concentrate compositions of pendimethalin comprise on a weight to volume basis, about 5.0% to 50.0% pendimethalin, wherein 4.0% of the pendimethalin crystals are the orange crystal form, most preferred 10.0% or more of the pendimethalin crystals are the orange crystal form. Further, the compositions of the present invention also comprise, on a weight to volume basis, about 0% to 50.0% of one or more secondary pesticide(s) being water soluble or having a melting point greater than 70° C.; about 0.5% to 1.0% antifoaming agents; about 2.0% to 20.0% antifreezing agent; about 2.0% to 20.0% surfactants dispersing agents, wetting agents, or mixtures thereof; about 0.05% to 3.0% thickening agents; about 0.01% to 1.0% preservatives; and the remainder water to total the compositionn to 100%.

Coformulants

Pesticides suitable for use in the compositions of the present invention include ureas, triazines, imidazolinones, alone or in combination, amongst just a few. Fungicides, insecticides and plant growth regulators which have melting points greater than 70° C. and/or possess physical properties which are amenable to the preparation of aqueous suspension concentrate compositions also may be used in the compositions of the present invention.

Additionally, water soluble pesticides, such as difenzoquat, amine salts, alkali or alkali metal salts of ioxynil, bromoxynil, phenoxy acetic acids, and imidazolinyl carboxylic acids such as 2-(4-isopropyl-4-methyl-5-oxo-2-imidazolin-2-yl)-3-quinolinecarboxylic acid and the like may readily be incorporated into the stable aqueous suspension concentrate compositions of this invention.

Preferred such higher melting components for use in the aqueous suspension compositions of the invention containing pendimethalin include: Isoproturon, [N,N-dimethyl-N'-(4-(1-methylethyl)-phenyl)urea]; Linuron, [N-(3,4-dichlorophenyl)-N'-methoxy-N'-methyl urea]; Metoxuron, [N'-(3-chloro-4-methoxyphenyl)-N,N-dimethylurea]; Chlortoluron, [N'-(3-chloro-4-methylphenyl)-N,N-dimethylurea]; Atrazine, [2-chloro-4-ethylamino-6-isopropylamino-1,3,5-triazine; other secondary active components include terbutylazine, 2-tert-butylamino-4-chloro-6-ethylamino-1,3,5-triazine and metolachlor, 2-chloro-6'-ethyl-N-(2-methoxy-1-methylethyl)acet-o-toluidide; Imidazolinone herbicides such as 2-(4-isopropyl-4-methyl-5-oxo-2-imidazolin-2-yl)-3-quinolinecarboxylic acid and water soluble salts thereof, and the isomeric mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)toluate.

Surfactants (including dispersing agents and/or wetting agents) suitable in the aqueous suspension compositions of the invention containing solid pendimethalin include: ethylene oxide/propylene oxide condensates; alkyl, aryl- and aryl, arylethoxylates and derivatives thereof; lignosulfonates; cresol- and naphthalene-formaldehyde condensates and sulfonates; polycarboxylates and derivatives thereof; and mixtures thereof.

In general, anionic polymerics, such as cresol formaldehyde condensates and their sulfonates, naphthalene formaldehyde condensates and their sulfonates and lignosulfonates have been found to minimize crystal formation during storage and as such are most preferred.

Suspending agents such as polysaccharide gums like Xanthan gum, guar gum; gum arabic and cellulose derivatives and the like are suitable for addition in amounts of about 0.02% to 3.0%, on a weight to volume basis.

Preservatives to prevent microbial spoiling in the compositions of the invention are included as necessary. One example is a 38% formaldehyde solution. Other preservatives include methyl or propyl parahydroxybenzoate, 2-bromo-2-nitro-propane-1,3-diol, sodium benzoate, glutaraldehyde, O-phenylphenol, benzisothiazolinones, 5-chloro-2-methyl-4-isothiazolin-3-one, pentachlorophenol, 2-4-dichlorobenzylalcohol, or mixtures thereof and others known to those in the art. Siliconic antifoaming agents are useful in the present compositions.

Antifreezing agents such as ethylene glycol, propylene glycol, other glycols, glycerine or urea may be added to the aqueous suspension concentrate compositions. Additional surfactants, preservatives and thickening agents, such as clays, precipitated silicas, polyvinyl alcohol, polyvinyl-pyrrolidone, polyacrylamides and the like, may then be added, as can higher melting active components or a suspension concentrate containing other active components.

Process of Manufacturing

Surprisingly, it has been found that stable aqueous suspension concentrate compositions of pendimethalin are prepared with at least 4.0% of the pendimethalin in the orange crystal form, contrary to what has been reported previously. In the present invention pendimethalin even in the large orange crystal form may be used to formulate stable aqueous suspensions. Further, up to 100% of the pendimethalin may be present as the orange crystal form when preparing the compositions of the invention, whereas only the yellow crystal form was favored to avoid large elongated crystals of formulates of pendimethalin.

Thus, aqueous suspension concentrate compositions of pendimethalin alone or in combination with a second higher melting pesticide(s) comprise on a weight to volume basis, about 5.0% to 50.0% of pendimethalin containing about 4.0% to 100% of the orange crystal form; about 0% to 50.0% of one or more secondary peticide(s) having a melting point greater than 70° C. or being water soluble; about 3.0% to 30.0% coformulants as described hereinabove; and the remainder water to total the composition to 100%.

The compositions of the present invention are readily prepared by adding solid pendimethalin to water that may contain some of the coformulants, such as the antifoaming agents and/or suspending agents; milling at ambient temperature the resulting solid-aqueous mixture to obtain an average particle size of less than 20 microns, preferably 2 microns to 10 microns; and then adding, if desired, other coformulants such as thickening agents, antifreezing agents, surfactants, dispersing agents, wetting agents, suspending agents and preservatives.

The following examples further illustrate the present invention and are not limitative thereof.

EXAMPLES 1-9

Preparation of stable aqueous suspension concentrate compositions of pendimethalin An aqueous solution containing surfactant(s) and antifoaming agents, and if desired, water soluble pesticides is prepared at ambient temperatures. Solid pendimethalin, having a minimum of 4% of the orange crystal form, is added, and any other solid second pesticide having a melting point greater than 70° C. may also be added.

This is milled to achieve the desired average particle size of suspended particles of less than 20 microns, preferably less than 6 microns (2 microns to 6 microns). Then thickening agents, suspending agents, antifreezing agents, preservatives and additional surfactants are admixed with the resulting mixture. Finally, this resulting stable aqueous suspension concentrate composition is packaged.

Utilizing the above procedure yields the stable aqueous suspension concentrate compositions listed in Table I.

TABLE I

Stable aqueous suspension concentrate compositions (% w/v)

| Composition | Example 1 | 2 | 3 | 4 | 5 | 6 | 7 | 8 | 9 |
|---|---|---|---|---|---|---|---|---|---|
| Pendimethalin - (orange/yellow ratio) | 23.6 (32/68) | 23.6 (32/68) | 23.6 (32/68) | 23.6 (24/76) | 23.6 (16/84) | 23.6 (8/92) | 23.6 (4/96) | 20.0 (46/54) | 44.8 (100%) |
| Isoproturon | 23.6 | 23.6 | 23.6 | 23.6 | 23.6 | 23.6 | 23.6 | — | — |
| Chlortoluron | — | — | — | — | — | — | — | 30.0 | — |
| Na+ cresol-formaldehyde sulphonated condensate | 3.0 | 3.0 | — | 3.0 | 3.0 | 3.0 | 3.0 | 3.0 | — |
| Na+ naphthalene sulfonated condensate | — | — | — | — | — | — | — | — | 3.0 |
| Ethylene oxide - propylene oxide copolymer | 2.0 | — | — | — | — | — | — | 2.0 | — |
| Na+ lauryl sulphate | — | 0.5 | — | 0.5 | 0.5 | 0.5 | 0.5 | — | — |
| Triethanolamine salt of polyarylarylethylene oxide phosphate | — | — | 3.0 | — | — | — | — | — | — |
| Ethylene glycol | 8.0 | — | 8.0 | 8.0 | 8.0 | 8.0 | 8.0 | 8.0 | 3.0 |
| Urea | — | 8.0 | — | — | — | — | — | — | — |
| Silica | 2.0 | 2.0 | 2.0 | 2.0 | 2.0 | 2.0 | 2.0 | 2.0 | 0.8 |
| Siliconic antifoam | 0.5 | 0.5 | 0.5 | 0.5 | 0.5 | 0.5 | 0.5 | 0.5 | — |
| Formaldehyde 38% solution | 0.125 | 0.25 | 0.25 | 0.25 | 0.25 | 0.25 | 0.25 | 0.25 | — |
| Xanthan gum | 0.05 | 0.1 | 0.1 | 0.1 | 0.1 | 0.1 | 0.1 | 0.05 | — |
| Water | QS | QS | QS | QS | QS | QS | QS | QS | QS |

What is claimed is:

1. An aqueous suspension concentrate composition comprising, on a weight to volume basis: about 5.0% to 50.0% solid pendimethalin having 4% orange crystal form to 96% yellow crystal form to 100% orange crystal form; about 3.0% to 30.0% non-pesticidal coformulants; and about 20.0% to 92.0% water.

2. A composition according to claim 1, wherein said coformulants are surfactants, dispersing agents or wetting agents; suspending agents; antifreezing agents; antifoaming agents; thickening agents; and preservatives.

3. A composition according to claim 2 wherein said surfactants, dispersing agents or wetting agents are ethylene oxide/propylene oxide condensates; alkyl, aryl- or aryl, aryl-ethoxylates; lignosulfonates; cresol-formaldehyde condensates or sulfonates thereof; naphthalene-formaldehyde condensates or sulfonates thereof; polycarboxylates or derivatives thereof; or mixtures thereof.

4. A composition according to claim 3, wherein the suspending agents are polysaccharide gums or cellulose derivatives.

5. A composition according to claim 4, wherein said polysaccharide gums are Xanthan gum, guar gum, gum arabic, or mixtures thereof.

6. A composition according to claim 5, wherein the antifreezing agents are ethylene glycol, propylene glycol, glycerine, urea, or mixtures thereof.

7. A composition according to claim 6, wherein the thickening agents are clays, precipitated silicas, polyvinyl alcohol, polyvinylpyrrolidone, polyacrylamides, or mixtures thereof.

8. A composition according to claim 7 wherein the preservative is a 38% formaldehyde solution, methyl or propyl parahydroxybenzoate, 2-bromo-2-nitro-propane-1,3-diol, sodium benzoate, glutaraldehyde, O-phenylphenol, benzisothiazolinones, 5-chloro-2-methyl-4-isothiazolin-3-one, pentachlorophenol, 2-4-dichlorobenzylalcohol, or mixtures thereof.

9. A composition according to claim 8, wherein the antifoaming agent is a siliconic antifoaming agent.

10. A composition according to claim 9, comprising, on a weight to volume basis: about 5.0% to 50.0% solid pendimethalin with 10%, on a weight to weight basis, of the orange crystal form; about 2.0% to 20.0% cresol-formaldehyde condensates or sulfonates thereof, naphthalene-formaldehyde condensates or sulfonates thereof; lignosulfonates, or mixtures thereof; about 0.05% to 2.5% Xanthan gum, guar gum, gum arabic, or cellulose derivatives; about 2.0% to 15.0% ethylene glycol, propylene glycol or urea; about 0.05% to 1.0% antifoaming agent; about 0.05% to 2.0% thickening agent; about 0.05% to 2.5% preservative; and the remainder water to total said composition to 100%.

11. A composition according to claim 10, comprising, on a weight to volume basis: about 20.0% to 40.0% pendimethalin; about 3.0% to 5.0% sodium cresol-formaldehyde condensate or sodium cresol-formaldehyde sulphonated condensate; about 5% to 10% ethylene glycol or urea; about 0.1% to 1.0% siliconic antifoaming agent; about 0.1% to 0.3% Xanthan gum; about 0.2% to 1.0% of a 38% formaldehyde solution; and about 48.3% to 79.4% water.

12. A composition according to claim 11, comprising, on a weight to volume basis: 40.0% pendimethalin; 5.0% sodium cresol-formaldehyde sulphonated condensate; 8.0% ethylene glycol; 0.5% siliconic antifoaming agent; 0.2% Xanthan gum; 0.5% of a 38% formaldehyde solution; and 51.4% water.

* * * * *